United States Patent
Bayon et al.

(10) Patent No.: US 6,596,304 B1
(45) Date of Patent: Jul. 22, 2003

(54) METHOD FOR PREPARING TWO-LAYER BICOMPOSITE COLLAGEN MATERIAL FOR PREVENTING POST-OPERATIVE ADHESIONS

(75) Inventors: Yves Bayon, Villeurbanne (FR); Philippe Gravagna, Irigny (FR); Jean-Lois Tayot, La Tour de Salvagny (FR)

(73) Assignee: Imedex Biomateriaux, Chaponost (FR)

(*) Notice: Subject to any disclaimer, the term of this patent is extended or adjusted under 35 U.S.C. 154(b) by 0 days.

(21) Appl. No.: 09/554,509

(22) PCT Filed: Sep. 16, 1999

(86) PCT No.: PCT/FR99/02212

§ 371 (c)(1),
(2), (4) Date: Jul. 11, 2000

(87) PCT Pub. No.: WO00/16821

PCT Pub. Date: Mar. 30, 2000

(30) Foreign Application Priority Data

Sep. 18, 1998 (FR) ............................................. 98 11701

(51) Int. Cl.⁷ ......................... A61L 15/16; C12N 11/02; C12M 5/06; C12M 5/08; C08H 1/00
(52) U.S. Cl. ..................... 424/444; 426/93.7; 426/426; 435/177; 435/395; 530/356; 530/402
(58) Field of Search ................................. 435/174, 177, 435/180, 182, 395, 397, 398, 402; 524/423, 426, 444, 93.7; 530/356, 402, 812; 606/151; 600/41

(56) References Cited

U.S. PATENT DOCUMENTS 5,201,745 A * 4/1993 Tayot et al. ................. 604/151
6,391,939 B2 * 5/2002 Tayot et al. ................. 523/105

FOREIGN PATENT DOCUMENTS

WO    WO 93/10731    * 6/1993
WO    WO 98/34656    * 8/1998

* cited by examiner

*Primary Examiner*—David M. Naff
(74) *Attorney, Agent, or Firm*—Larson & Taylor PLC

(57) ABSTRACT

A bicomposite material based on collagen is prepared which has two closely bound layers and is biocompatible, non-toxic, hemostatic and biodegradable in less than a month, and can be used in surgery to achieve hemostasis and prevent post-surgical adhesion. To prepare the material, a solution of collagen or gelatin, which may contain glycerine and a hydrophilic additive such as polyethylene glycol or a polysaccharide, is poured onto an inert support to form a layer 30 μm to less than 100 μm thick. Then a polymeric porous fibrous layer is applied during gelling of the collagen or gelatin, and the resultant material is dried. The polymeric porous fibrous layer may be made of collagen or a polysaccharide, and have a density of not more than 75 mg/cm², a pore size from 30 μm to 300 μm and a thickness of 0.2 cm to 1.5 cm.

30 Claims, 2 Drawing Sheets

A — film
B — compress

A - film
B - compress

METHOD FOR PREPARING TWO-LAYER BICOMPOSITE COLLAGEN MATERIAL FOR PREVENTING POST-OPERATIVE ADHESIONS

FIELD OF THE INVENTION

The present invention concerns a bicomposite material based on collagen, which is biocompatible, non-toxic and biodegradable, comprising uniquely or mainly a layer forming a collagenic film and a layer forming a fibrous polymer compress or sponge with a high level of porosity.

The material according to the invention can be used in surgery, notably in visceral surgery, and is specifically applied for the simultaneous achievement of hemostasis and prevention of post-surgical adhesion, while promoting the healing of the injured tissue.

DESCRIPTION OF THE RELATED ART

Patents FR-A-2 628 634 and U.S. Pat. No. A-5,201,745 (IMEDEX) describe patches for use in visceral surgery made of a biomaterial consisting of two layers of collagen superposed and closely associated, these being a porous adhesive layer of fibrous collagen and a collagen film or collagenic material such as gelatine.

In this type of material, the film seals the membrane or patch and increases mechanical cohesion, also helping to prevent the formation of post-operative adhesions. The porous layer of fibrous collagen notably plays the part of a hemostatic compress.

A double-layered collagenic membrane has been proposed in patent applications EP-A-O 686 402 and WO 96/08277 (COLETICA) with the aim of obtaining anti-adhesive properties.

The collagens and collagenic materials used in such patches or membranes may be obtained from native collagen or from different types of atelocollagens or pepsin-treated collagens, notably type I bovine collagens, and type I, III, III+I and IV human collagens. These collagens can be partly oxidized, for example to increase their adhesive power, and the layer forming the film may include other materials, mixed with the collagenic material, used, for example to strengthen its mechanical resistance and improve its anti-adhesion properties. It is not easy to produce these patches or membranes, however. Indeed, on the one hand it is essential to guarantee an excellent bond between the layer forming the film and the layer forming the fibrous compress, while retaining each layer's individuality on the other. Also, when the layer of fibrous material is brought into contact with the liquid collagenic material destined to form the film, on contact with the liquid, the collagenic fibres tend to become impregnated so that an excellent bond is indeed obtained between the two layers but it is very difficult to control formation of the film and respect the porosity of the supporting layer.

For this purpose, it has been proposed (FR-A-2 628 634), to pour the collagenic material which is to form the film, onto a layer of fibrous collagen which has first been slightly compressed to limit interpenetration between the two layers.

It has also already been proposed (EP-A-O 686 402) to freeze the porous fibrous layer so that it is hydrated and impermeable and pour the liquid collagenic material destined to form the film onto this layer so as to eliminate interpenetration between the two layers, but this level of prevention of interpenetration gives rise to cohesion defects.

The process described also gives rise to a two-layer collagengelatine membrane which has been dried or freeze-dried in one piece, which prevents an impermeable film and a highly porous layer from being formed simultaneously. It is also recommended to compress this membrane.

Hemostatic sponges composed of native bovine collagen are commercially available, as for example Colgen® (Immuno AG), Pangen® (Fournier) and Surgicoll® (Biodynamics); but these are not covered on one side with an impermeable film, acting as a barrier and they have several disadvantages:

i) left in the body, they can generate adhesions;
ii) the blood diffuses through preferential routes in the compress, reducing the area of contact of the collagen with the platelets and consequently the hemostatic effect of the compress;
iii) they no longer have a hemostatic effect on strongly bleeding wounds (ruptured arterioles for example), because the blood passes through the compress;
iv) generally produced from acid collagen, they are difficult to handle because they strongly stick to surgical instruments or latex gloves.

Other more complex products such as TachoComb® (Nycomed) combining collagen, fibrinogen, thrombin and aprotinin provide better hemostasis than collagen sponges, but these products are likely to facilitate the development of post-operative adhesions. They contain thermolabile enzymes and must be stored between 2 and 8° C. The multiplication of components of human or animal origin is also a handicap, because of problems of traceability and registration linked to these products, leading to prohibitive excess cost.

From the point of view of preventing post-operative adhesions, this is particularly difficult with haemorrhagic wounds, especially where bleeding is widespread (Buckman et al., J. Surg. Res., 1976, 20 1–5; Wiseman et al., J. Reprod. Med., 1992, 37, 766–770). Bleeding from wounds strongly affects the efficacy of the products marketed and used to prevent adhesion, such as INTERCEED® TC7 (Johnson & Johnson) (Wiseman et al., J. Reprod. Med., 1992, 37, 766–770). Indeed it can lead to the deposit of fibrin on the anti-adhesive film and then facilitate the development of post-operative adhesions. This results in the necessity to perform the most complete hemostasis possible, using thrombin or any other technique, before applying products such as INTERCEED® TC7 to haemorrhagic wounds. Therefore to prevent adhesions it is advantageous to develop materials which also have hemostatic properties.

SUMMARY OF THE INVENTION

The present invention therefore aims to considerably perfect the previously described bicomposite collagenic materials, and to improve their hemostatic properties considerably, while retaining and, if necessary, even improving their properties which aim to prevent post-operative adhesions.

The invention also aims to provide a hemostatic bicomposite collagenic material which can, in addition, prevent post-operative adhesions and facilitate healing.

Another of the invention's aims is to produce such a material which particularly promotes colonization by the body's specific cells and is likely to be completely biodegradable within a short time and easy to control by making simple changes to the manufacturing process.

The invention also aims to provide a biocompatible bicomposite material which is non-toxic and not sticky to the touch when dry, to facilitate handling, but which can develop adhesive properties in a physiological environment, in particular in contact with blood.

Another of the invention's aims is to provide a particularly economic process to obtain such a bicomposite material.

Therefore the invention aims to produce a bicomposite collagenic material which is biocompatible, non-toxic and biodegradable in less than a month, characterized in that it comprises solely or principally two closely linked layers, these being a layer forming a film based on a collagenic constituent, notably collagen which has at least partially lost its helical structure, or gelatine, and a layer forming a porous compress, substantially uncompacted, based on a polymer constituent.

As well as the collagenic constituent, the film preferably comprises at least one macromolecular hydrophilic additive which does not react chemically with collagen.

The second layer can be made of a porous compress, substantially uncompacted, of non-denatured collagen.

The invention also aims to provide a preferred process for producing these materials.

This process is based on the discovery that, when a liquid solution based on a collagenic constituent destined to form a film is left to gel, there is an instant, during gelling, when the porous layer of polymer constituent forming the compress can be laid on the surface of the gelling material, and the under part of the said porous layer partly penetrates the gel, while at least partly retaining a structure which guarantees almost perfect adhesion between the film to be constituted and the porous layer, while preserving almost all the individual properties of the porous layer and the film.

The inventors noted most surprisingly that:

the collagen film can be formed by dehydration of the liquid layer of collagen in spite of the presence of a freeze-dried porous layer on top of it;

the upper porous layer is not degraded or changed by association with the film in the process of formation.

The invention therefore aims to provide a process for obtaining a bicomposite material according to the invention, characterized in that a solution of collagenic constituent is poured onto a suitable inert support, to a thickness destined to form a film, and in that a substantially uncompacted compress made of a polymer constituent is applied onto the said solution during gelification, and then in that the material obtained is dried or left to dry.

DETAILED DESCRIPTION OF THE INVENTION

Figure 1:
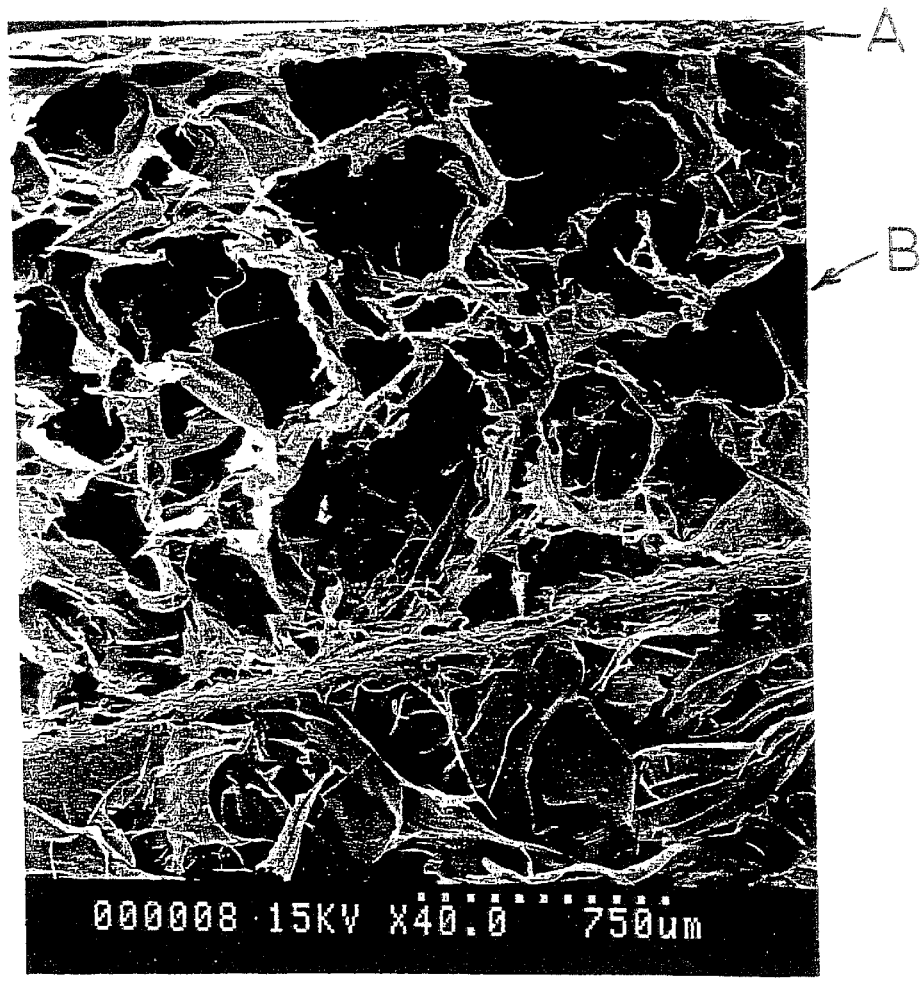
FIG. 1 is a photograph illustrating structures of the bicomposite material depicting a specimen of Example 7 in accordance with the present invention.

The process according to the invention will be described in greater detail below:

To implement this process, an aqueous solution of the collagenic constituent destined to form the film of the above-mentioned bicomposite material is prepared.

According to the invention, the term "collagenic constituent" preferably designates collagen which has at least partially lost its helical structure through heating or any other method, or gelatine.

The term "gelatine" here includes commercial gelatine made of collagen which has been denatured by heating and in which the chains are at least partially hydrolyzed (molecular weight lower than 100 kDa).

The collagenic constituent used for the purposes of the invention is preferably formed of non-hydrolyzed collagen, mainly composed of α chains (molecular weight around 100 kDa).

In the context of the invention α chains means complete α chains or fragments of these complete α chains produced by the loss of a small number of amino acids.

The term "non-hydrolyzed" as used according to the invention means that less than 10% of the collagenic chains has a molecular weight below about 100 kDa.

If heating is used to denature the helical structure of the collagen, the heating must be moderate and provided under gentle conditions so as to avoid degradation by hydrolytic cleavage of the gelatine thus formed.

Commercial gelatine can be used for the invention but is not preferred.

The collagen used can be of human or animal origin. It may particularly be type I bovine collagen, or type I or type III human collagen or mixtures in any proportions of the last two types.

Native collagen is used by preference, in acid solution or after processing, to eliminate the telopeptides, notably by pepsin digestion.

The collagen can also be modified by oxidative cleavage. For this purpose periodic acid or one of its salts can be used, applying the technique described by M. TARDY et al. (FR-A-2 601 371 and U.S. Pat. No. 4,931,546).

It is recalled briefly that this technique consists of mixing the collagen in acid solution with a solution of periodic acid or one of its salts at a concentration of between 1 and $10^{-5}$ M, preferably between $5 \cdot 10^{-3}$ and $10^{-1}$ M, at a temperature of between 10 and 25° C. for 10 minutes to 72 hours.

This process breaks down some of the collagen's components, these being hydroxylysine and the sugars, thus creating reactive sites without causing crosslinking.

The oxidative cleavage of collagen allows moderate cross-linking later in the collagenic material but the invention does not exclude the possibility of providing this function by other means of moderate cross-linking, for example by beta or gamma irradiation, or other agents of moderate cross-linking, for example chemical reagents at suitably low and non-toxic doses.

For some applications, the film part of the bicomposite material according to the invention, is made of collagen which is not oxidized or a mixture in any proportions of non-oxidized and oxidized collagens.

In a preferred embodiment of the invention, a solution of collagenic constituent as defined above is used, and this may be partially or completely modified by oxidative cleavage, giving a collagen concentration of 5 to 50 g/l. The collagen or gelatine concentration is preferably 30 g/l.

The solution of oxidized collagen, non-oxidized collagen or a mixture thereof, thus prepared, is heated, for example to a temperature in excess of 37° C., preferably to a temperature of between 40 and 50° C., for at least one hour. This results in the collagen's helical structure being at least partially denatured.

A final preparation can notably be obtained which is similar to gelatine but with a molecular weight of elementary chains equal or greater than 100 kDa.

Heating the collagen solution to a temperature above 37° C. leads to the gradual loss of the collagen's helical structure, but the invention does not exclude the possibility of achieving this by other physical or chemical means, for example by ultrasonication, or by the addition of chaotropic agents.

According to a variant of the invention, at least one macromolecular hydrophilic additive is added to the previous preparation, this being preferably chemically unreactive with the collagenic constituent.

"Chemically unreactive with the collagenic constituent" here means a hydrophilic compound which is not likely to react with the collagen present, notably which does not form covalent bonds with it during cross-linking.

The macromolecular hydrophilic additive according to the invention advantageously has a molecular weight in excess of 3,000 Daltons.

It may consist of synthetic hydrophilic polymers, preferably of a molecular weight between 3,000 and 20,000 Daltons. Polyethylene glycol is particularly preferred.

It may also consist of polysaccharides, of which starch, dextran and cellulose can be mentioned.

Oxidized forms of these polysaccharides can also be used, revealing carboxylic functions in these molecules.

Mucopolysaccharides can also be used for the purposes of the invention, but are not preferred because their particular animal origin makes them difficult to prepare so that they meet the standards of traceability.

The hydrophilic additive is selected according to various parameters, notably concerning its application, price, safety, biodegradability and/or ease of elimination.

The concentration of hydrophilic additive(s) is 2 to 10 times less than that of the collagenic constituent.

According to a variant execution of the invention, glycerine is added to the mixture of collagenic constituent/hydrophilic additive(s).

In this case, the concentration of glycerine is advantageously between 3 and 8 g/l, not exceeding one third of the collagenic constituent concentration.

In the collagenic preparation, the concentrations of collagenic constituent, hydrophilic additive(s) and glycerine, when present, are preferably between 2 and 10% for the collagenic constituent, 0.6 and 4% for the hydrophilic additive(s) and 0.3 and 2.5% for glycerine respectively.

The collagenic preparation is fluidised at a temperature of 30 to 50° C.

It is advantageously neutralized to a neutral pH to avoid hydrolyzing the collagen by heating and to obtain a film of physiological pH while permitting pre-cross-linking of the collagen if the mixture contains oxidized collagen as indicated previously.

For implementation of the process according to the invention, a substantially non compacted porous compress, based on a polymer constituent is also prepared.

The term "polymer constituent" according to the invention means a fibrous, non toxic polymer with hemostatic and/or healing properties. It may be non-denatured collagen or collagen which has at least partially lost its helical structure through heating or any other method, consisting mainly of non-hydrolyzed α chains, of molecular weight close to 100 kDa. It may also consist of polysaccharides such as chitin or chitosan, or polysaccharides modified by oxidation of alcohol functions into carboxylic functions such as oxidized cellulose.

The term "non-denatured collagen" means collagen which has not lost its helical structure.

The collagen used for this second layer of bicomposite material according to the invention, consists of native collagen or atelocollagen, notably as obtained through pepsin digestion and/or after moderate heating as defined previously.

These may have been previously chemically modified by oxidation, methylation, succinylation or any other known process.

The origin and type of collagen are as indicated for the film described above.

The term "substantially non compacted porous compress" means a compress made of polymer fibres with a porous structure such as is obtained by freeze-drying for example, or an even more porous compress which can then have been slightly compacted.

Defined in another form, the said layer forming a porous compress has a density of not more than 75 mg/cm$^2$ and preferably below 20 mg/cm$^2$.

Figure 2:
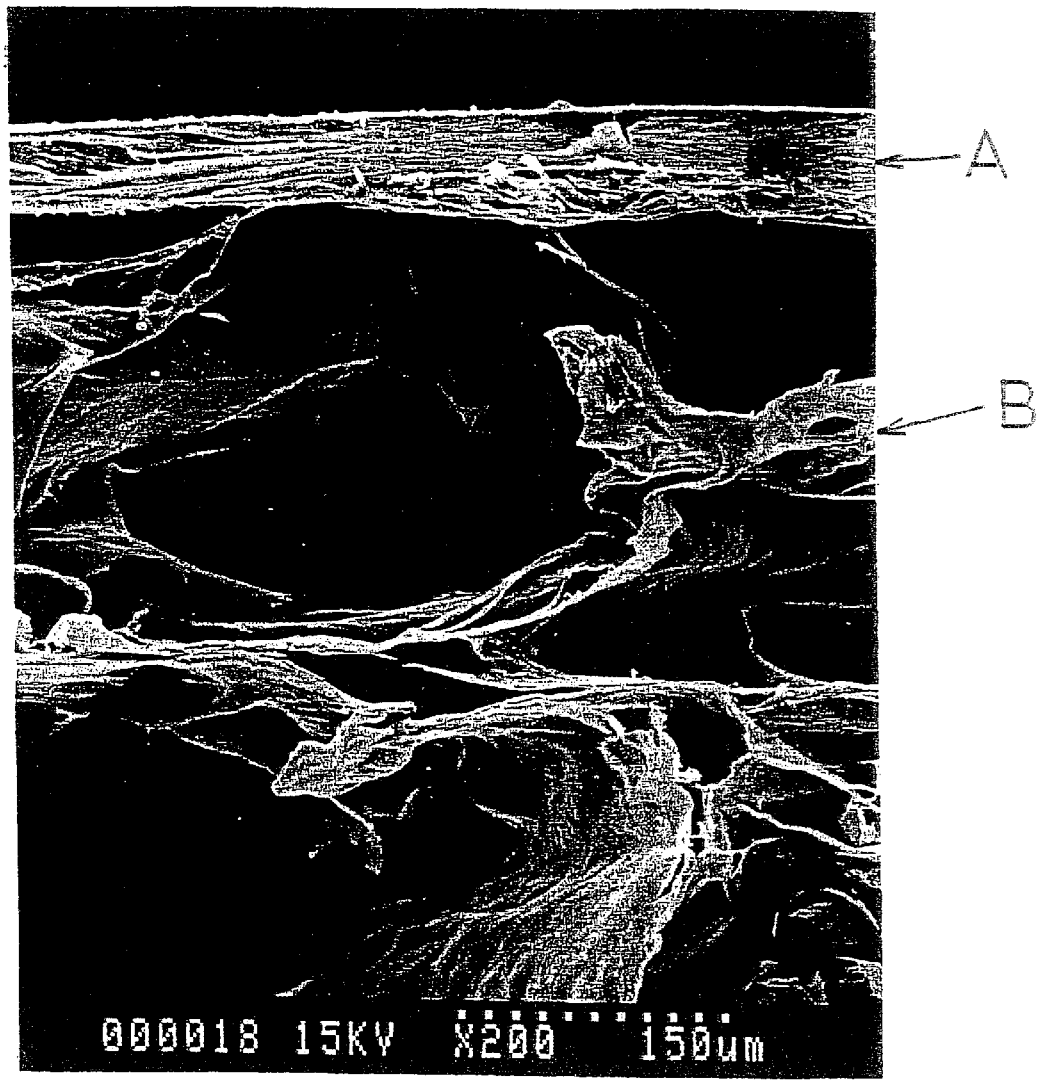
FIG. 2 is a photograph showing a specimen of Example 7 made from the compress as in Example 3 with the film being produced as in Example 8 in accordance with the present invention.

The porosity of these materials is illustrated in FIGS. 1 and 2.

The size of the pores varies from 20 to 300 µm and is generally between 100 and 200 µm.

The porous compress can be obtained preferably by freeze-drying, from an aqueous acid solution of collagen at a concentration of 2 to 50 g/l and a temperature of 4 to 25° C. The concentration of collagen is preferably 10 g/l.

This solution is advantageously neutralized to a pH of around 7 to 8.

The porous compress can also be obtained by freeze-drying a fluid foam prepared from a solution of collagen or heated collagen, emulsified in the presence of a volume of air in variable respective quantities (volume of air:water varying from 1 to 10).

The porous fibrous layer made of a polymer constituent is preferably at least 0.2 cm thick and is particularly preferred between 0.3 and 1.5 cm thick.

The actual bicomposite material is prepared by assembling the film-forming layer and the porous compress as detailed below.

In its simplest method of implementation, the process according to the invention involves pouring the solution of collagenic constituent, destined to form the film, possibly containing the hydrophilic additive(s) and glycerine, onto an adequate, substantially flat support, distributing it evenly.

The support is inert in that it does not react with the above-mentioned components and is not involved in the cross-linking process. It is preferably hydrophobic, for example, PVC or polystyrene.

However, this support can also consist of a strippable material which will remain slightly adhesive and which can then be separated at the time of surgical use.

This support may itself also consist of a film, for example dried collagen, onto which the solution is poured, or a layer of collagenic material gel in a distinctly more advanced state of gelification.

The density of the thin layer applied is preferably between 0.1 and 0.3 g/cm$^2$.

This collagenic solution is poured at a temperature advantageously between 4 and 30° C., and preferably between 18 and 25° C.

This solution is left to gel and a porous compress prepared as indicated above is applied to the said solution during gelification.

Application of the porous layer onto the solution during gelification means laying the porous layer onto the gel, with application continuing by simple gravity or optionally, by slight compression but not enough to cause any significant compaction of the porous layer.

The moment at which the porous layer is applied to the solution during gelification is such that the gel is still soft and allows the porous layer or compress to penetrate over a distance which is advantageously around 0.05 to 2 mm and preferably around 0.1 to 0.5 mm.

This moment can be determined empirically by applying compresses or bits of compresses to the gel at various times.

Generally, when the solution which is gelling is at a temperature of between 4 and 30° C., the porous layer is applied 5 to 30 minutes after the solution has been poured over the surface holding it.

It is left to dry or dried in order to obtain the bicomposite material according to the invention.

When the collagenic solution destined to form the film includes oxidized collagen, it is polymerized while the bicomposite material is drying.

This drying occurs favourably at a temperature of 4 to 30° C., preferably between 18 and 25° C.

The material can be dried in a jet of sterile air if necessary.

After drying, the bicomposite material according to the invention can be separated from its support. In a variant, it may include or incorporate a film or layer of collagenic material onto which the collagenic solution has been poured.

The process described above may be implemented in a similar way using other types of hemostatic compresses, notably compresses such as are available commercially. Examples of these are compresses based on oxidized cellulose (Surgicel® or Interceed® compresses) or those based on chitin or chitosan.

The bicomposite material according to the invention is stable at ambient temperature and remains stable for long enough to be handled at temperatures which may rise to 37–40° C.

The film of collagenic material is preferably less than 100 μm thick, and more preferably between 30 and 75 μm.

The porous compress is preferably between 0.2 cm and 1.5 cm thick, and still more preferably between 0.3 cm and 1.2 cm.

According to the envisaged applications, the bicomposite material conforming to the invention can be subjected to various routine processes such as sterilization, etc.

Sterilization is favourably provided by irradiation with beta (electronic irradiation) or gamma (irradiation using radioactive cobalt) rays.

The bicomposite material according to the invention can be used as it is or cut to sizes appropriate for the envisaged application.

The present invention has led to the production of bicomposite materials in which a layer of fibrous polymer, notably non-denatured collagen, which is extremely porous and may be very thick, to form an efficient compress or sponge, is very closely bound to a thin collagenic film, which is well delimited and has suitable properties and dimensions.

It was then established that such a two-layer material displayed a set of particularly surprising hemostatic, anti-post-operative adhesion and biodegradability qualities.

The biomaterial obtained is easy to handle. It does not stick to surgical instruments or gloves when dry.

It displays acceptable mechanical resistance while retaining a certain flexibility, provided by the hydrophilic elements in the film of composite material.

The material according to the invention is a local hemostatic, the active principle of which is the polymer constituent, notably non-denatured collagen or oxidized cellulose, which contributes, like endogenous collagen, to the hemostatic and healing process. It is preferably applied with pressure to the site of haemorrhage until hemostasis is obtained. The blood is absorbed by the porous layer of material and concentrated under the material with the film of material acting as a seal barrier. On contact with the polymer, it is transformed into a hemostatic plug and/or a clot.

The material very quickly adheres to the bleeding wound, through the formation of a hemostatic plug and/or clot by the polymer.

It is thought that the considerably improved hemostatic properties of the compress according to the invention are notably due to the possibility of absorbing a very large quantity of blood while preventing it from spreading either transversally or in the plane of the biomaterial. In addition, the diffusion of blood through the porous compress, within the area marked by the wound, increases the area of contact between the hemostatic substance and the platelets. It thus accelerates hemostasis by playing on the various ways of obtaining coagulation, the final phase of which leads to the formation of a network of platelets and fibrin reinforcing the compress's adhesion to the wound.

On the contrary, the two-layer collagenic materials of the prior art described above, are insufficiently porous so that the blood cannot penetrate. This favours the lateral leakage of blood under the compress which does not provide good adhesion. Because of this, it is much harder to stop the bleeding.

The bicomposite collagenic material according to the invention is particularly suitable for preventing post-operative adhesion, particularly in bleeding wounds, because the film prevents adherence, the composite material providing good adhesion in such wounds and there is no blood at the interface.

Apart from their hemostatic properties and the prevention of post-operative adhesions, the collagenic material of the present invention facilitates healing because of its composite structure, combining a highly porous polymer layer and a collagenic film.

The porous part of the material can easily be colonized by the surrounding cells. The film protects the healing wound for several days as it forms a barrier to bacteria and micro-organisms.

The power of the film of the material to prevent adhesion is also reinforced by the polymer used for the porous layer of material accelerating healing of the wound.

According to the invention, the bicomposite collagenic material is therefore useful for hemostasis and the prevention of post-operative adhesions on bleeding wounds, while facilitating healing.

In addition, the macromolecular hydrophilic additive is eliminated by diffusion through the collagenic material, in a few days, the swelling of this material promoting degradation of the collagenic film in less than a month.

The bicomposite material according to the invention can also be used to promote healing. Its very open porous structure promotes rapid cellular colonization. The film isolates the porous part to make it accessible to specific cells.

As an example, fibroblasts can be cultured in the porous part of the material, in vitro, and epithelial cells can be cultured on the film making two temporarily separate compartments.

However, although this is not preferred, a film of collagenic constituent and a non-compacted porous compress can be bound by a biocompatible, biodegradable and non toxic adhesive agent, so long as this agent can provide a sufficiently strong bond between the film and the compress, although it is only present in small quantities.

Examples of adhesive agents are surgical glues, notably fibrin and collagenic glues described in the patent Tardy et al. U.S. Pat. No. 5,618,551 and application WO 98/15299.

This invention will now be described in detail with the aid of non-limiting examples showing different possible combinations of the materials and their hemostatic powers and ability to prevent post-operative tissular adhesions.

According to the invention, a compress can be made which is then cut to the size and shape required, or a biomaterial prepared which has the size and shape of the patch required.

EXAMPLES

Example 1

Preparation of Collagen Compresses With a Neutral pH:

The collagen used is type I bovine collagen, extracted from calf dermis, and possibly rendered soluble through pepsin digestion and, purified by saline precipitation, using the techniques already described. Type I or type III human collagen or a mixture of these in any proportions can be used in the same way.

A 10 g/l solution of collagen is prepared by dissolving 23 g of damp collagen (12% humidity) in 2070 g of ultrafiltered water, at an ambient temperature below 25° C. It is neutralized using sodium hydroxide to a neutral pH, which leads to precipitation of the collagen.

The suspension is then poured onto freeze-dry plates, with 0.5 to 1 g/cm$^2$ and dehydrated by freeze-drying, using one cycle lasting about 24 hours.

Finally, in a variant, the freeze-dried collagen compress can be heated to 60° C. for several hours (4 to 15) which provides it with better cohesion and mechanical resistance in certain applications.

Example 2

Preparation of Collagen Compresses With a pH of 5–5.5:

The preparation of collagen compresses with a pH 5–5.5 helps to limit the collagen precipitation phenomenon. It is prepared as in example 1, the only difference being the neutralization of the collagen solution with sodium hydroxide at a pH close to collagen's isoelectric point, i.e. 5 and 5.5.

Example 3

Preparation of Collagen Compresses With an Acid pH:

Slightly acid compresses are prepared as in example 1, the only difference being that the collagen solution is not neutralized, which avoids any collagen precipitation.

Example 4

Preparation of a Solution of Oxidized Collagen:

The 30 g/l oxidized collagen used for this example, is prepared according to patent FR-A-2 715 309. Type I bovine collagen is used, extracted from calf dermis by solubilization at an acid pH, or pepsin digestion, and purified by saline precipitation according to the techniques already described.

The products marketed by COLLAGEN Corp. under the names VITROGEN® or ZYDERM®, may be used in this application.

Dry collagen fibres are used for preference, obtained by precipitation of an acid solution of collagen by adding NaCl, then washing and drying the precipitate obtained using aqueous solutions of acetone in concentrations increasing from 80% to 100%.

Type I or type III human collagen or any mixture of these can be used In the same way.

The 30 g/l solution of collagen is prepared by dissolving it in 0.01 N HCl. Its volume is 49 liters. Periodic acid is added to it at a final concentration of 8 mM, i.e. 1.83 g/l. Oxidation takes place at an ambient temperature close to 22° C. for 3 hours away from light.

Then an equal volume of a solution of sodium chloride is added to the solution to obtain a final concentration of 41 g/l NaCl.

After waiting for 30 minutes, the precipitate is collected by decantation through a fabric filter, with a porosity close to 100 microns, then washed 4 times with a 41 g/l solution of NaCl in 0.01 N HCl. This produces 19 kg of acid saline precipitate. This washing process eliminates all traces of periodic acid or iodine derivatives during oxidation of the collagen.

Then, several washes in an aqueous solution of 80% acetone are used to concentrate the collagen precipitate and eliminate the salts present.

A final wash in 100% acetone is used to prepare 3.6 kg of a very dense acetone precipitate of acid, oxidized, non-reticulated collagen, with no trace of undesirable chemical products.

The acetone paste is diluted with apyrogenic distilled water at 40° C., to obtain a 3% concentration of collagen, for a volume of 44 liters. This suspension of oxidized collagen is used to prepare porous compresses in a similar way to examples 1,2 and 3.

Example 5

Preparation of a Solution of Heated Collagen:

A collagen gel of neutral pH and concentration close to 50 g/l is heated to 45° C. for 10 minutes to fluidify it.

4 volumes of air or other gas are incorporated into the solution of heated collagen through 2 syringes mounted opposite each other and connected to produce the emulsion, by successively pulling and pushing the plungers, which mix the respected contents of each syringe evenly.

The emulsion is prepared on freeze-dry plates and gelled by cooling, then frozen and freeze-dried.

Example 6

Preparation of a Solution of Oxidized, Heated Collagen Designed to Form a Film

The suspension of a volume of 44 liters described in example 4, is heated for 30 minutes at 50° C., then filtered under sterile conditions through a membrane of 0.45 micron porosity in a drying oven at 40° C.

As soon as this solution is homogeneous and at 35° C., a sterile concentrated solution of PEG 4000 (polyethylene glycol with a molecular weight of 4000 Daltons) and glycerine is added to it to produce a final concentration of 0.9% PEG, 0.54% glycerine and 2.7% oxidized collagen.

As soon as these additions have been made, the pH of the solution is adjusted to 7.0 by adding a concentrated solution of sodium hydroxide.

Example 7

Preparation of a Solution Including a Mixture of Non-oxidized, Heated Collagen and Oxidized Collagen, Designed to Form a Film:

A variant of the preparation of collagen solution used for the film, is to take heated non-oxidized collagen or a mixture of heated oxidized collagen, prepared as in example 6, and heated non-oxidized collagen, in any proportions.

The collagen used for preparing non-oxidized, heated collagen is type I bovine collagen, extracted from calf dermis, possibly solubilized by pepsin digestion and purified by saline precipitation using the techniques already described. Type I or type III human collagens or mixtures of these in any proportions can be used in the same way.

A 30 g/l solution of non-oxidized, heated collagen is prepared by dissolving 65.2 g of damp collagen (12% humidity) in 1940 g of ultrafiltered water at 42° C. A sterile concentrated solution of PEG 4000 (polyethylene glycol with a molecular weight of 4000 Daltons), glycerine and possibly oxidized, heated collagen prepared as in example 6 is added to this solution at 42° C. to produce a final concentration of 0.9% PEG, 0.54% glycerine and 2.7% total collagen. The pH of the solution is adjusted to 7.0, by adding a concentrated solution of sodium hydroxide.

Example 8
Preparation of an Acid Solution of Non-oxidized Heated Collagen Designed to Form a Film:

An acid solution of heated, non-oxidized collagen, for the film, is prepared as in example 7, with the following differences:
i) the collagen used is only non-oxidized heated collagen, the preparation of which is described in example 1;
ii) the mixture used for the film, of which the final concentrations of PEG, glycerine and collagen are 0.9%, 0.54% and 2.7% respectively, is acid.

Example 9
Preparation of a Bicomposite Material From a Collagen Compress:

The collagen solution destined to form the film, as described in examples 4 to 7, is poured in a thin layer with a density of 0.133 g/cm$^2$ on a flat hydrophobic support such as PVC or polystyrene, at an ambient temperature close to 22° C.

A collagen compress, prepared as in examples 1, 2 or 3 is applied uniformly to the solution of heated collagen, 5 to 20 minutes after it was poured onto the support. This waiting time is the collagen solution gelling time, required for application of the collagen compress, to prevent it dissolving or becoming partially hydrated in the liquid collagen.

Penetration of the compress into the gelled collagen solution is judged to be less than 0.5 mm.

The material is then dehydrated in a jet of sterile air, at ambient temperature, which leads to evaporation in about 18 hours.

The bicomposite material obtained is easy to remove from the support.

It can be cut to the dimensions required for the application concerned, without weakening it.

The bicomposite material is then put into an airtight double polyethylene bag.

The unit is sterilized by gamma irradiation or electron beam (beta) irradiation at a dose of between 25 and 35 KGy.

The material is stable at ambient temperature.

The presence of glycerine in the material essentially helps to make the film more flexible and facilitates its use. The material can be prepared without glycerine.

The use of PEG 4000 as macromolecular hydrophilic agent is not limiting. PEG 3000, PEG 6000 or polysaccharides such as soluble starch (OSI, France) and Dextran T40 (Pharmacia Fine Chemicals, Sweden) can be used instead.

FIGS. 1 and 2 are photographs taken under scanning electron microscope, enlarged by 40 and 200 times respectively, illustrating the structures of the bicomposite material prepared as indicated above.

FIG. 1 shows a specimen of example 9 made from the compress as in example 1 prepared from pepsinated collagen, the film being produced as in example 6.

FIG. 2 shows a specimen of example 9 made from the compress as in example 3, the film being produced as in example 8.

Example 10
Preparation of a Bicomposite Material Using an Oxidized Cellulose Compress:

The procedure is the same as for example 9 but using a porous compress based on oxidized cellulose as is available on the market under the name Interceed® or Surgicel®.

What is claimed is:

1. A method for obtaining a bicomposite material which has two closely bound layers and is bicompatible, non-toxic and biodegradable in less than one month, said method comprising the steps of:
   (i) pouring a solution of collagen or gelatin onto an inert support so as to form a 30 $\mu$m to less than 100 $\mu$m-thick layer;
   (ii) applying to the solution during gelling of the collagen or gelatin a polymeric porous fibrous layer having a density of no more than 75 mg/cm$^2$, a pore size from 20 $\mu$m to 300 $\mu$m and a thickness of 0.2 cm to 1.5 cm; and
   (iii) drying or leaving to dry the material obtained from step (ii) to provide said bicomposite material.

2. The method according to claim 1, wherein the solution of collagen in step (i) has a concentration of collagen of between 5 and 50 g/l.

3. The method according to claim 2, wherein the solution of collagen in step (i) is an acid solution of native collagen.

4. The method according to claim 1, wherein the solution of collagen in step (i) includes collagen modified by oxidative cleavage.

5. The method according to claim 4, wherein the solution of collagen in step (i) is modified by treatment with periodic acid or one of its salts.

6. The method according to claim 1, wherein the solution of collagen in step (i) is heated to a temperature of between 40° and 50° C.

7. The method according to claim 1, wherein at least one macromolecular hydrophilic additive; chemically unreactive with respect to the collagen or gelatin, is added to the solution of collagen in step (i).

8. The method according to claim 7, wherein the concentration of hydrophilic additive(s) is 2 to 10 times less than the concentration of collagen in the solution in step (i).

9. The method according to claim 7, wherein glycerine is added to the solution of collagen in step (i).

10. The method according to claim 9, wherein the concentration of glycerine is between 3 and 8 g/l and does not exceed one third of the concentration of collagen of the solution in step (i).

11. The method according to claim 1, wherein the collagen solution in step (i) is an aqueous solution containing 2 to 10% of collagen or gelatin, 0.6 to 4% of hydrophilic additive(s) and 0.3 to 2.5% of glycerine.

12. The method according to claim 1, wherein the solution in step (i) is neutralized.

13. The method according to claim 1, wherein the support in step (i) is a PVC or polystyrene support.

14. The method according to claim 1, wherein the solution in step (i) has a density of between 0.1 and 0.3 g/cm$^2$.

15. The method according to claim 1, wherein the collagen or gelatin solution in step (i) is poured at a temperature of 4 to 30° C.

16. The method according to claim 1, wherein the polymeric porous fibrous layer in step (ii) is made of collagen.

17. The method according to claim 16, wherein the polymeric porous fibrous layer of step (ii) is prepared from an aqueous acid solution of collagen, the concentration of which is 2 to 50 g/l when the collagen is not denatured.

18. The method according to claim 17, wherein the aqueous acid solution of collagen is neutralized to a pH of around 7 to 8.

19. The method according to claim 17, wherein the solution of collagen used to prepare the polymeric porous fibrous layer of step (ii) is freeze-dried.

20. The method according to claim 19, wherein the solution of collagen used to prepare the polymeric porous fibrous layer of step (ii) is spread in a layer with a density of between 0.2 and 1.5 mg/cm² for freeze-drying.

21. The method according to claim 1, wherein the polymeric porous fibrous layer of step (ii) is made of polysaccharide.

22. The method according to claim 1, wherein the polymeric porous fibrous layer of step (ii) is made of polysaccharide modified by oxidation of the alcohol functions into carboxylic function.

23. The method according to claim 1, wherein, when the polymeric porous fibrous layer is applied to the solution of collagen or gelatin during gelling, the polymeric porous fibrous layer of step (ii) is allowed to penetrate for around 0.05 to 2 mm in the gel which is forming.

24. The method according to claim 1, wherein the material obtained is dried in a jet of sterile air in step (iii).

25. The method according to claim 1, wherein the polymeric porous fibrous layer is produced by freeze-drying a collagenic emulsion and a gas.

26. The method according to claim 1, wherein the material obtained is sterilized in step (iii).

27. The method according to claim 7, wherein the macromolecular hydrophilic additive has a molecular weight of between 3,000 and 20,000 Daltons.

28. The method according to claim 7, wherein the macromolecular hydrophilic additive is polyethylene glycol.

29. The method according to claim 7, wherein the hydrophilic additive is chosen from the group consisting of polysaccharides and mucopolysaccharides.

30. The method according to claim 7, wherein the hydrophilic additive is an oxidized polysaccharide.

* * * * *